United States Patent
Ouchi

(10) Patent No.: US 7,681,434 B2
(45) Date of Patent: Mar. 23, 2010

(54) SENSING DEVICE

(75) Inventor: Toshihiko Ouchi, Sagamihara (JP)

(73) Assignee: Canon Kabushiki Kaisha, Tokyo (JP)

( * ) Notice: Subject to any disclaimer, the term of this patent is extended or adjusted under 35 U.S.C. 154(b) by 450 days.

(21) Appl. No.: 11/632,958

(22) PCT Filed: Aug. 10, 2006

(86) PCT No.: PCT/JP2006/316125

§ 371 (c)(1),
(2), (4) Date: Jan. 19, 2007

(87) PCT Pub. No.: WO2007/026544

PCT Pub. Date: Mar. 8, 2007

(65) Prior Publication Data

US 2008/0314152 A1    Dec. 25, 2008

(30) Foreign Application Priority Data

Aug. 30, 2005 (JP) .............................. 2005-248561

(51) Int. Cl.
*G01N 21/17* (2006.01)
*G01N 21/59* (2006.01)
*G01N 21/61* (2006.01)

(52) U.S. Cl. .............. 73/31.06; 250/370.01; 250/341.1; 250/338.1; 356/36

(58) Field of Classification Search .................... None
See application file for complete search history.

(56) References Cited

U.S. PATENT DOCUMENTS

| | | | |
|---|---|---|---|
| 4,537,510 A * | 8/1985 | Takahasi | 356/435 |
| 5,586,131 A | 12/1996 | Ono et al. | 372/19 |
| 5,659,560 A | 8/1997 | Ouchi et al. | 372/27 |
| 5,699,373 A | 12/1997 | Uchida et al. | 327/27 |
| 5,764,670 A | 6/1998 | Ouchi | 372/45 |
| 5,789,750 A * | 8/1998 | Nuss | 250/338.1 |
| 7,248,995 B2 | 7/2007 | Itsuji et al. | 702/159 |

(Continued)

FOREIGN PATENT DOCUMENTS

JP    62-25486 U    2/1987

(Continued)

OTHER PUBLICATIONS

M. Nagel, et al., "Integrated THz technology for label-free genetic diagnostics", Applied Physics Letters, vol. 80, No. 1, Jan. 2002, pp. 154-156.

(Continued)

*Primary Examiner*—Hezron Williams
*Assistant Examiner*—Rose M Miller
(74) *Attorney, Agent, or Firm*—Fitzpatrick, Cella, Harper & Scinto

(57) ABSTRACT

The present invention provides a sensing device for obtaining information of a test sample using an electromagnetic wave including a frequency region within a frequency region of 30 GHz to 30 THz, the sensing device comprising an electromagnetic wave transmitting portion including a plurality of transmission portions (4a, 4b) for propagating electromagnetic waves and detection portions (3a, 3c) for receiving and detecting the electromagnetic waves from the plurality of transmission portions (4a, 4b), in which at least one of the plurality of transmission portions (4a, 4b) is constructed such that the test sample (5, 6) can be placed in a portion affected by an electromagnetic wave propagating therethrough.

7 Claims, 5 Drawing Sheets

U.S. PATENT DOCUMENTS

| | | | |
|---|---|---|---|
| 7,463,104 B2 * | 12/2008 | Sekiguchi et al. | 331/107 SL |
| 2003/0226969 A1 * | 12/2003 | Williamson | 250/341.1 |
| 2005/0110495 A1 * | 5/2005 | Kitagawa | 324/321 |
| 2006/0016997 A1 * | 1/2006 | Siegel et al. | 250/339.11 |
| 2006/0039431 A1 | 2/2006 | Sekiguchi et al. | 372/44.01 |
| 2006/0045807 A1 * | 3/2006 | Zhang et al. | 422/82.05 |
| 2006/0085160 A1 | 4/2006 | Ouchi | 702/150 |
| 2006/0188398 A1 | 8/2006 | Yano et al. | 422/82.01 |
| 2006/0197021 A1 | 9/2006 | Ouchi | 250/343 |
| 2006/0214176 A1 | 9/2006 | Ouchi et al. | 257/98 |
| 2006/0215167 A1 * | 9/2006 | O'Gorman et al. | 356/454 |
| 2006/0227340 A1 | 10/2006 | Shioda et al. | 356/614 |
| 2006/0244629 A1 | 11/2006 | Miyazaki et al. | 340/855.7 |
| 2007/0030115 A1 | 2/2007 | Itsuji et al. | 340/5.8 |
| 2007/0195921 A1 | 8/2007 | Ouchi | 378/1 |
| 2007/0215808 A1 | 9/2007 | Sekiguchi et al. | 250/339.01 |
| 2007/0229094 A1 | 10/2007 | Kasai et al. | 324/639 |
| 2007/0235718 A1 | 10/2007 | Kasai et al. | 257/21 |
| 2007/0252604 A1 | 11/2007 | Ouchi et al. | 324/637 |

FOREIGN PATENT DOCUMENTS

| | | |
|---|---|---|
| JP | 4-27494 B2 | 5/1992 |
| JP | 10-104171 | 4/1998 |
| JP | 2005-227021 | 8/2005 |
| WO | WO 03100396 A1 * | 12/2003 |
| WO | 2005/001505 | 1/2005 |

OTHER PUBLICATIONS

D. Mittleman, "T-ray Imaging: New Possibilities in the Far Infrared", IEEE MTT-S International Microwave Symposium Digest, 2002, vol. 3, pp. 1575-1578.

U.S. Appl. No. 11/751,517, filed May 21, 2007 by Yasushi Koyama, Takeaki Itsuji and Toshihiko Ouchi.

U.S. Appl. No. 11/833,781, filed Aug. 3, 2007 by Toshihiko Ouchi and Ryota Sekiguchi.

* cited by examiner

SENSING DEVICE

TECHNICAL FIELD

The present invention relates to a sensing device and method for obtaining information of, for example, properties of a target test sample using an electromagnetic wave including a frequency region principally within a millimeter-wave to terahertz-wave region (30 GHz to 30 THz).

BACKGROUND ART

In recent years, nondestructive sensing techniques using an electromagnetic wave of millimeter-wave to terahertz (THz) wave frequencies (30 GHz to 30 THz) have been under development. An example of techniques now under development in application fields of the electromagnetic wave of such a frequency band is an imaging technique using a safe fluoroscopic apparatus alternative to an X-ray fluoroscope. In addition, examples of techniques now under development include a spectral technique for obtaining an absorption spectrum or complex dielectric constant of a material to examine the bonding state therein, a technique for analyzing biomolecules, and a technique for estimating a carrier concentration or mobility.

Up to now, a photoconductive device including antennas also serving as electrodes which are provided on a photoconductive film formed on a substrate is suitably used as an example of a THz wave generating means (see JP 10-104171 A). FIG. 8 shows a structural example of the photoconductive device. A substrate 130 has, for example, a silicon-on-sapphire structure treated with radiation. In the substrate 130, a silicon film which is a photoconductive material is formed on a sapphire substrate. An LT-GaAs film grown on a GaAs substrate at a low temperature is used as the photoconductive film in many cases. A dipole antenna 138 formed in a surface of the substrate includes a pair of dipole feeders 138a and 138b and a pair of dipole arm portions 139a and 139b. A light pulse is focused on a gap 133. When a voltage is applied across the gap 133, a THz pulse generates. When a light current is detected without the application of the voltage across the gap 133, the THz pulse can be detected. Here, the photoconductive device is a detector 132. The light current is detected by a current amplifier 134. A substrate lens 136 has a function of conducting coupling from a slab mode (substrate mode) of an electromagnetic wave confined in the substrate 130 to a radiation mode to free space, and a function of controlling a radiation angle of an electromagnetic wave propagation mode in space.

The above-mentioned structure is an example in which the electromagnetic wave is propagated through a space using a single photoconductive device. There has been also proposed a small functional device in which a semiconductor thin film serving as a photoconductive device and transmission paths for causing generated electromagnetic waves to propagate are integrated on a single substrate (see Applied Physics Letters, Vol. 80, No. 1, 7 Jan., 2002, pp. 154-156). FIG. 9 is a plan view showing the functional device. The functional device has a structure 164 in which a thin film composed of only a LT-GaAs epitaxial layer of the photoconductive device is transferred to a part of high-frequency transmission paths 165 and 163 formed on an Si substrate 160. In the structure 164, microstrip lines are formed on the substrate 160 so as to sandwich an insulator resin. A gap is produced in a part of the lines. The thin film of LT-GaAs is placed only under the gap. Driving is performed such that a laser beam is emitted from a surface side of the substrate 160 to the gap placed between metallic lines 161 and 165 through space propagation to propagate a generated THz electromagnetic wave to the lines. When a test sample 167 to be examined is applied to a filter region 166 having a resonant structure on the transmission paths, a change in propagation condition is detected from a portion 162 using an EO crystal. Therefore, the properties of the test sample 167 can be examined.

However, according to a method disclosed in Applied Physics Letters, Vol. 80, No. 1, 7 Jan. 2002, pp. 154-156, the amount of change in propagation condition of the terahertz-wave to the test sample is small. Therefore, a large amount of test sample is necessary. For the improvement of sensitivity, it is necessary to increase the strength of the electromagnetic wave. When a reference test sample is compared with a target test sample, it is necessary that data be obtained and stored for each step or that additional measurement be performed by sensing devices having different transmission paths. In this case, it is difficult to adjust a condition of measuring the reference test sample to the same condition as that of measuring the target test sample. Thus, it is difficult to accurately estimate the amount of change in the target test sample from the reference test sample.

DISCLOSURE OF THE INVENTION

In view of the above-mentioned circumstances, a sensing device according to the present invention serves to obtain information of a test sample using an electromagnetic wave including a frequency region in a frequency region of 30 GHz to 30 THz. The sensing device includes an electromagnetic wave transmitting portion having a plurality of transmission portions for propagating an electromagnetic wave therethrough and a detection portion for receiving and detecting the electromagnetic wave from the transmission portions. Here, at least one of the transmission portions is constructed such that a test sample can be placed in a portion affected by the electromagnetic wave propagating therethrough.

In view of the above-mentioned circumstances, a sensing method according to an aspect of the present invention allows sensing for obtaining the information of the test sample using the sensing device. The sensing method includes a detecting step of detecting electromagnetic waves propagating through the respective transmission portions by the detection portions with a test sample placed in at least one of the transmission portions of the electromagnetic wave transmitting portion; and a step of processing signals from the detection portions in the detecting step to obtain the information of the test sample. In this sensing method, the detecting step can be a step of detecting the electromagnetic waves propagating through the respective portions by the detection portions with a test sample placed in one of the transmission portions and with a reference test sample placed in another one of the transmission portions, and then a differential output is detected based on the signals from the detection potions in the detecting step to measure the property of the test sample.

According to the present invention, there are a plurality of transmission portions for separately propagating an electromagnetic wave including information of a test sample to be measured and an electromagnetic wave including information different from the information of the test sample. Therefore, a plurality of detection signals can be substantially simultaneously obtained. Thus, the detection signals are suitably processed (for example, comparison calculation is performed), so information of the properties or the like of the test sample can be obtained at relatively high speed with high sensitivity.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

BEST MODE FOR CARRYING OUT THE INVENTION

An embodiment of the present invention will be described with reference to FIG. 1. Implemented herein is a sensing device provided with a plurality of transmission paths for propagating principally a terahertz-wave as an electromagnetic wave therethrough to substantially simultaneously detect a test sample and a reference test sample and directly output a result obtained by comparison therebetween, thereby achieving improved sensitivity.

Figure 1:
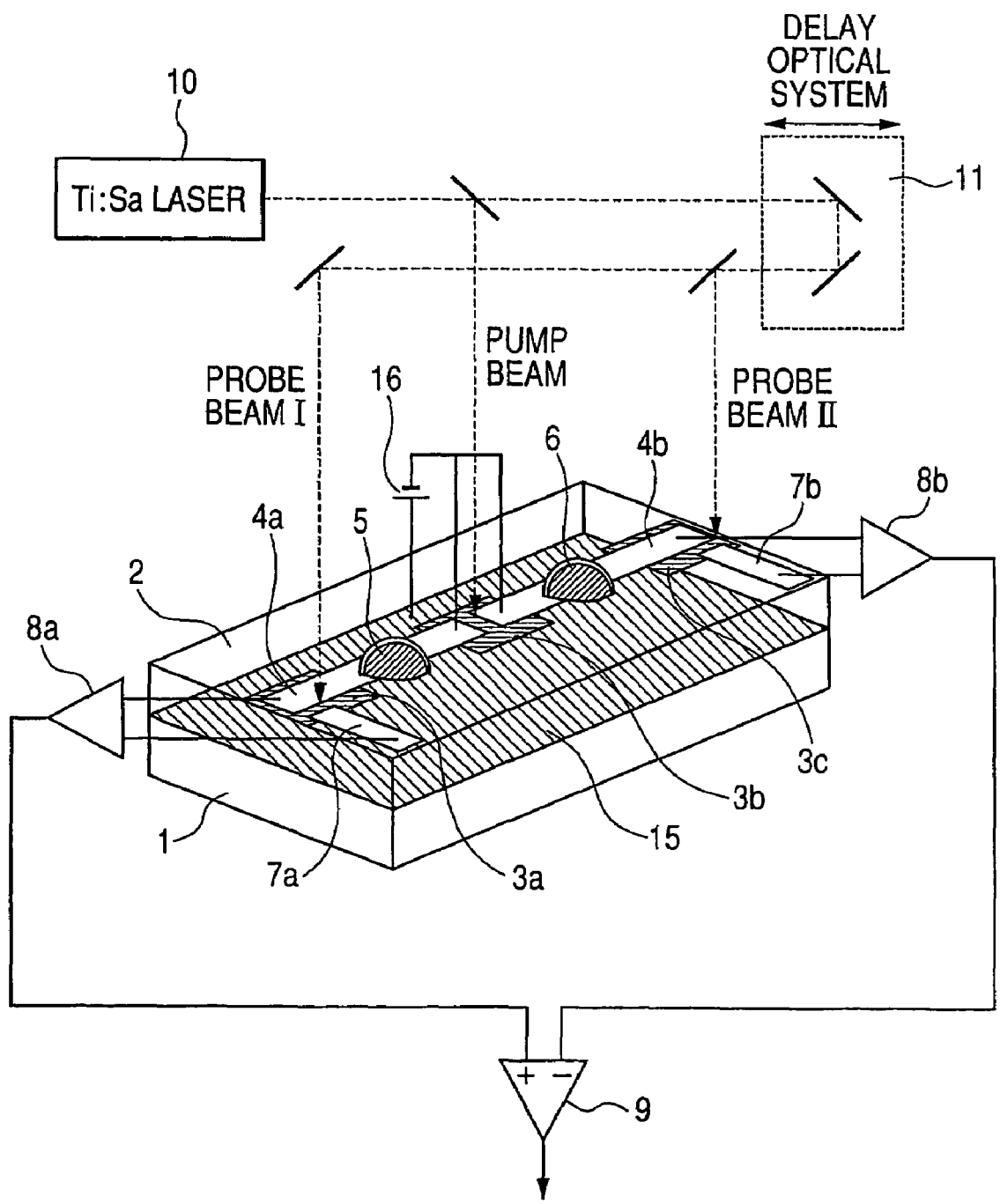
FIG. 1 is a perspective view showing a sensing device according to an embodiment and Example 1 of the present invention.

FIG. 1 is a perspective view showing a chip portion of the sensing device. In FIG. 1, transmission paths 4a and 4b are formed on a chip surface of the substrate 1. A portion in which a terahertz-wave is generated is a photoconductive switch element formed in a region to which a low-temperature-grown- (LT-) GaAs thin film 3b is transferred. An electromagnetic wave generated here propagates through the two transmission paths (transmission portions of an electromagnetic wave transmitting portion) 4a and 4b in mutually opposite directions. The terahertz-wave is generated by emitting an ultra-short pulse laser beam from a titanium sapphire laser 10 to the LT-GaAs thin film 3b to which an electric field is applied. The generated terahertz-wave is emitted in all directions, so an output in the case where the two transmission paths 4a and 4b are provided does not become smaller than that in the case where a single transmission path is provided. Therefore, the energy use efficiency is improved as compared with a conventional example as described in Applied Physics Letters, Vol. 80, No. 1, 7 Jan. 2002, pp. 154-156. When a generation source (electromagnetic wave generating portion) is placed in the center of a linear transmission path, the loss of an electromagnetic wave is small, so efficiency becomes extremely high. In this embodiment, such a structure is used.

Electromagnetic waves propagating in respective directions are detected by two LT-GaAs photoconductive switches formed in regions to which LT-GaAs thin films 3a and 3c are transferred, similarly to the electromagnetic wave generating portion. Respective output currents from the switches are converted into voltages by amplifiers 8a and 8b and then a difference between outputs from the amplifiers 8a and 8b is calculated by a comparator device 9. Therefore, a common phase noise can be removed, so a difference between test samples 5 and 6 applied onto the transmission paths 4a and 4b can be detected with high sensitivity. The test samples 5 and 6 are placed in portions affected by the electromagnetic waves propagating through the transmission paths.

When one of the test samples 5 and 6 is placed as a reference test sample, a slight difference between the reference test sample and the test sample to be measured can be obtained. That is, the reference test sample is placed on at least one of the transmission paths. A signal is detected by a detection portion different from that for the test sample to be examined and then an output is obtained by comparison between a plurality of signals, so a slight change can be obtained with high sensitivity. Therefore, a very small amount of test sample can be precisely measured. The reference test sample and the test sample are simultaneously examined, so high-speed examination can be performed.

As described above, in this embodiment, the plurality of transmission paths and the detection portions corresponding thereto are provided on the same substrate. Suitably used as the transmission path is a microstrip line, a coplanar line, a coplanar strip line, or a single line which can be formed on a surface of the substrate. A transmission path configuration to be suitably used is such a shape that the transmission paths are linearly extended from the generation source in to directions, such a type that a transmission path is Y-branched at a point thereof, or the like. When three or more transmission paths are used, the transmission paths may be radially extended from the generation source. In this case, for example, the test sample is placed on a transmission portion, the reference test sample is placed on another transmission portion, and no test sample is placed on the other transmission portion. With this configuration, electromagnetic waves can be detected from the respective transmission portions. In this embodiment, the electromagnetic wave transmitting portion is composed of the plurality of separate transmission paths. The electromagnetic wave transmitting portion can be also composed of a plurality of transmission paths having a common part (see an example shown in FIG. 3) or a plurality of space portions which are separated from each other or have a common part (see examples shown in FIGS. 6 and 7).

The electromagnetic wave generating portion coupled to the transmission paths may be placed in the outside or integrated on the same substrate. A system in which an electromagnetic wave is distributed from a single generation portion to a plurality of transmission paths or that in which a plurality of generation portions may be provided corresponding to the transmission paths may be employed. It is preferable that electromagnetic waves propagating from the generation portion to the respective transmission portions of the electromagnetic wave transmitting portion be correlated with each other and have coherent characteristics. A choice of generation portions includes, in addition to the photoconductive switch element for generating a terahertz pulse in response to a femtosecond laser beam applied from the outside, for example, a resonant tunnel diode or a quantum cascade laser which can be oscillated by current injection. When the laser is applied, a choice of detectors includes a photoconductive switch element. When the current injection is performed, a choice of detectors includes, for example, a Schottky barrier diode.

Means for placing a test sample include one which simply performs an application on a surface by ink jet or the like and one which has a flow path for supplying a fluid to the vicinity of the transmission path.

As described above, the two or more transmission portions are set to difference states (that is, different test samples are placed on the plurality of transmission portions, respectively, while there may be the case where nothing is placed on one of the transmission portions). The electromagnetic waves from the respective transmission portions are substantially simultaneously detected by the detection portions. The detection signals are suitably processed (for example, comparison calculation is performed), so the information of the properties or the like of the test sample is obtained at relatively high speed with high sensitivity. Therefore, terahertz sensing can be performed. In contrast to this, it is necessary to separately measure the test samples in a conventional case.

EXAMPLES

Hereinafter, specific examples will be described.

Example 1

Example 1 will be described with reference to FIG. 1. In FIG. 1, a metal conductive layer 15 which becomes a ground plane and a dielectric 2 are formed on an Si substrate 1. LT-GaAs films 3a to 3c each having a thickness of approximately 2 μm and metal wirings 4a, 4b, 7a, and 7b are formed on the dielectric 2. For example, a Ti/Au layer can be used as the metal conductive layer 15, and BCB (product name: Cycloten) having a thickness of 5 μm can be used as the dielectric 2. The present invention is not limited to those.

The LT-GaAs films 3a to 3c are obtained as follows. A sacrifice layer of AlAs is grown on a GaAs substrate by an MBE method and then GaAs is grown at a low temperature of approximately 250° C. The grown GaAs film is peeled off from the AlAs layer and thus can be bonded onto the BCB dielectric 2. When only the LT-GaAs film 3b of the transferred LT-GaAs films is to be electrically connected with the ground plane 15, a through wiring (not shown) is formed. A voltage from a power source 16 can be applied between the metal wiring 4a and the ground plane 15 and between the metal wiring 4b and the ground plane 15 to vertically apply an electric field to the LT-GaAs film 3b. Each of the metal wirings 4a and 4b has a width of 5 μm and a length of 1 mm and is made of Ti/Au. The metal wirings 4a and 4b compose microstrip lines together with the ground plane 15 and act as transmission paths for an electromagnetic wave generated in the LT-GaAs film 3b. The transmission paths may be of coplanar lines or single lines in addition to the microstrip lines. A gap having a width of approximately 5 μm is formed on a surface of each of the LT-GaAs films 3a and 3c between the wirings 4a and 7a and between the wirings 4b and 7b to compose a photoconductive switch element.

When the sensing device is used, test samples 5 and 6 which become targets are applied onto the respective transmission paths 4a and 4b at controlled positions in controlled amounts by ink jet or the like. Propagation conditions of electromagnetic waves are changed by the presence of the test samples. A peak value of the terahertz pulse generated from the photoconductive switch element formed in the LT-GaAs film 3b reduces, a delay time thereof varies, and a waveform thereof changes, so the properties or the like of the test sample can be measured. For example, a current-to-voltage conversion amplifier (such as a transimpedance amplifier) can be used as each of the amplifiers 8a and 8b. A differential amplifier can be used as the comparator device 9.

Next, an operation of the entire sensing device will be described. A part of an output of a titanium sapphire laser 10 having a pulse width of approximately 100 fsec is applied to the LT-GaAs film 3b to generate a terahertz-wave pulse while an electric field of 2 V is applied to the LT-GaAs film 3b by the power source 16. The remaining part of the output passes through a delay optical system 11 and is distributed to the LT-GaAs films 3a and 3c. Timings when the terahertz-wave pulses are applied to the LT-GaAs films 3a and 3c are preferably adjusted in advance by the optical system such that the timings agree with each other by the correction of a delay time caused by a manufacturing error of the transmission paths 4a and 4b. To adjust the timings, it is only necessary to scan the delay optical system 11 in a condition where the test samples 5 and 6 are not present such that a differential output of the differential amplifier 9 becomes 0. This corresponds to an adjustment means for detecting a difference between delay times of the electromagnetic waves propagating through the transmission paths in advance with an initial state in which there are not the test sample and the reference test sample which are in contact with the transmission paths and correcting a difference between times for which the electromagnetic waves propagate through the respective transmission paths based on detected information. Thus, when a propagation condition difference, for example, a delay time, which is proper to the sensing device, is corrected in advance, the precision is improved.

A signal from the differential amplifier 9 in the case where the reference test sample is placed on only one of the transmission paths is stored in advance. In addition, a signal from the differential amplifier 9 in the case where there is not a test sample is compared with a signal from the differential amplifier 9 in the case where there is the test sample. Thus, the precision can be further improved.

Figure 2:
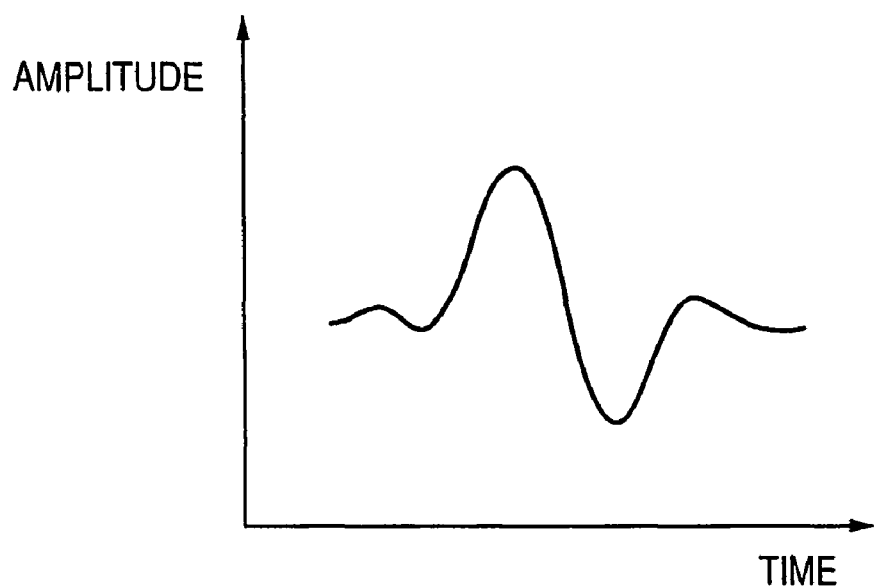
FIG. 2 is a graph showing an example of an output waveform from the sensing device shown in FIG. 1.

FIG. 2 shows an example of a waveform output from the differential amplifier 9 in the case where a DNA sample is used as a test sample. In this case, the test sample 5 has a double-strand structure in which a single-stranded DNA is applied onto the transmission path 4a so as to have a diameter of 200 μmϕ and a DNA which is a target is further applied thereto to achieve hybridization. On the other hand, the test sample 6 is a single-strand reference test sample in which the same single-stranded DNA is applied onto the transmission path 4b and no reaction is conducted. The double-strand structure has a different delay time, so the waveform as shown in FIG. 2 may be obtained as its differential output. A delay time difference is small, so an oscillation structure or the like is essential in the prior art. However, when the differential output is detected, a signal is obtained using a simple structure. As described above, when the signal obtained in the case where the test sample is placed on only one of the transmission paths is stored in advance, two original waveforms can be estimated from the differential output to perform Fourier analysis. When there is a specific fingerprint spectrum placed in the terahertz-wave region, the spectrum can be detected. When there is the resonance structure as described in Applied Physics Letters, Vol. 80, No. 1, 7 Jan., 2002, pp. 154-156, it is difficult to perform waveform analysis.

The case where one type of test sample is measured using a chip is described above. When a chip in which a plurality of transmission paths are arranged on the same substrate 1 in array is suitably scanned to apply a titanium sapphire laser beam to a desirable position of the generation portion, plural types of test samples can be measured using the chip. Even in such a case, high-speed measurement can be realized.

Example 2

An operation in Example 2 of the present invention is substantially identical to that in Example 1. A different point is that a metal wiring 22 is branched at a point thereof to form Y-branch transmission paths 27a and 27b as shown in a plan view of FIG. 3. At a generation portion 21a, a laser beam is applied to a gap portion between the wirings 22 and 23. The laser beam may be an ultra-short pulse laser beam of approximately 100 fsec as in the case of Example 1. An oscillating frequency difference of a THz order may be caused between two semiconductor lasers oscillated in a 830 nm band to apply a THz continuous wave of a single frequency as its beat signal.

Figure 3:
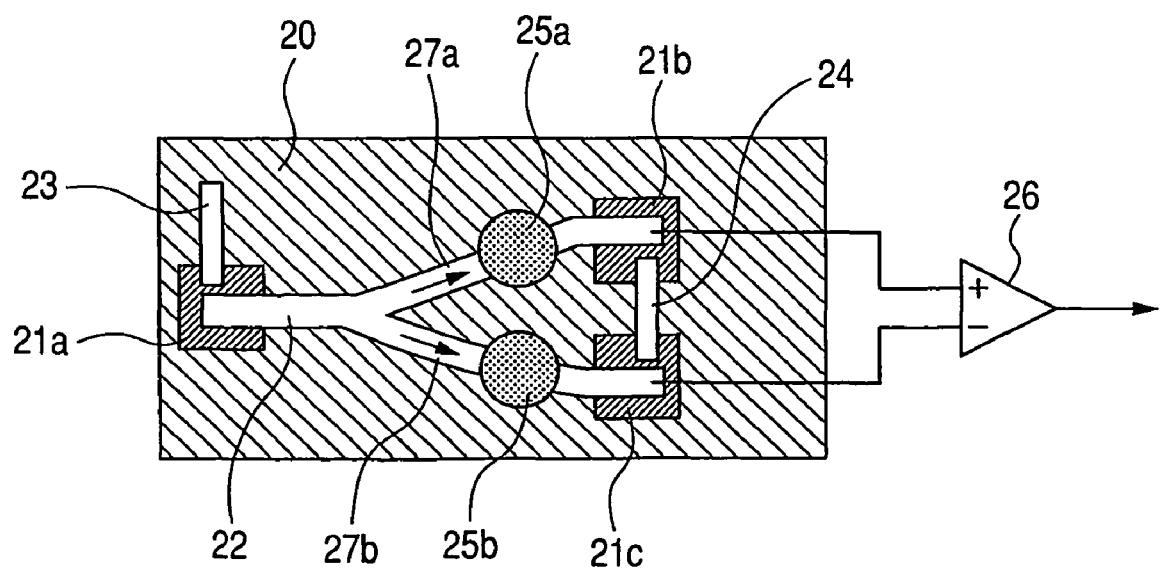
FIG. 3 is a plan view showing a sensing device according to Example 2 of the present invention.

A terahertz wave from the generation portion 21a is divided into two by the Y-branch transmission paths 27a and 27b. The two waves reach detection regions 21b and 21c in which photoconductive switch elements are formed to perform signal detection. At this time, balance reception using a differential amplifier 26 is performed for signal reception output. As in the case of Example 1, when a reference test sample 25a and a test sample 25b are applied to, for example, positions shown in the drawing, the sensitivity can be improved. Unlike Example 1, the terahertz wave is divided, so signal strengths decrease. However, the detection regions 21b and 21c can be placed close to each other and the test samples 25a and 25b can be placed close to each other, so an error caused by variations in positions of the respective portions is suppressed. In FIG. 3, reference numeral 20 denotes a substrate and 24 denotes a wiring having the same function as that of each of the wirings 7a and 7b described in Example 1.

Example 3

Figure 4:
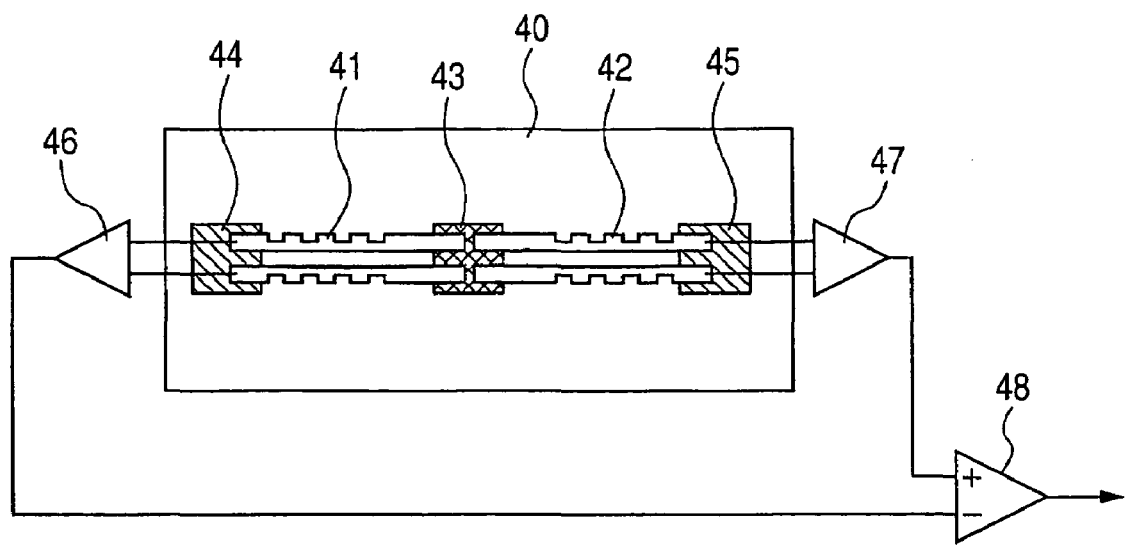
FIG. 4 is a plan view showing a sensing device according to Example 3 of the present invention.

Example 3 of the present invention uses a current injection terahertz oscillator element. Unlike the above-mentioned examples, it is unnecessary to apply a laser beam from the outside, so size of the sensing device can be significantly reduced. An optical adjustment mechanism is unnecessary, so cost can be reduced. FIG. 4 is a plan view showing the terahertz oscillator element. In this example, the transmission paths are formed as coplanar strip lines 41 and 42 having two lines provided on a surface of a substrate 40. Each of the lines 41 and 42 has a distributed Bragg reflector (DBR) structure to resonate at a specific frequency and also serves as a resonator for an oscillator 43. The oscillator 43 is designed such that a resonant tunnel diode (RTD) is used for a gain structure and a maximum gain peak is obtained at the vicinity of 1 THz. Therefore, even in the case of the DBR, a diffraction grating is formed such that a reflection strength becomes stronger at the vicinity of 1 THz. An electromagnetic wave oscillated by current injection to the oscillator 43 reaches detectors 44 and 45. A quantum cascade laser or the like may be used for the gain structure. In this example, each of the detectors 44 and 45 comprises a planer Schottky diode. Photocurrents generated corresponding to strengths of the reached electromagnetic waves are amplified by current amplifiers 46 and 47. A difference output is obtained by a differential amplifier 48.

In this example, not a pulse but a continuous wave is used, so the outputs of the detectors 44 and 45 reflect the strengths of reached continuous waves. In this structure, when the samples are placed on the transmission paths 41 and 42, the selected wavelength and reflectance of the DBR is changed with a variation in dielectric constant, thereby changing an oscillating state of the oscillator 43. Also, the ratio between the strengths of the electromagnetic waves outputted to the detectors 44 and 45 is changed by a difference between two test samples. Thus, the properties or the like of the test sample can be measured with high sensitivity.

This example is particularly effective in the case where a frequency at which the interference with a test sample is large is known and the presence or absence of the test sample is detected.

Example 4

Figure 5:
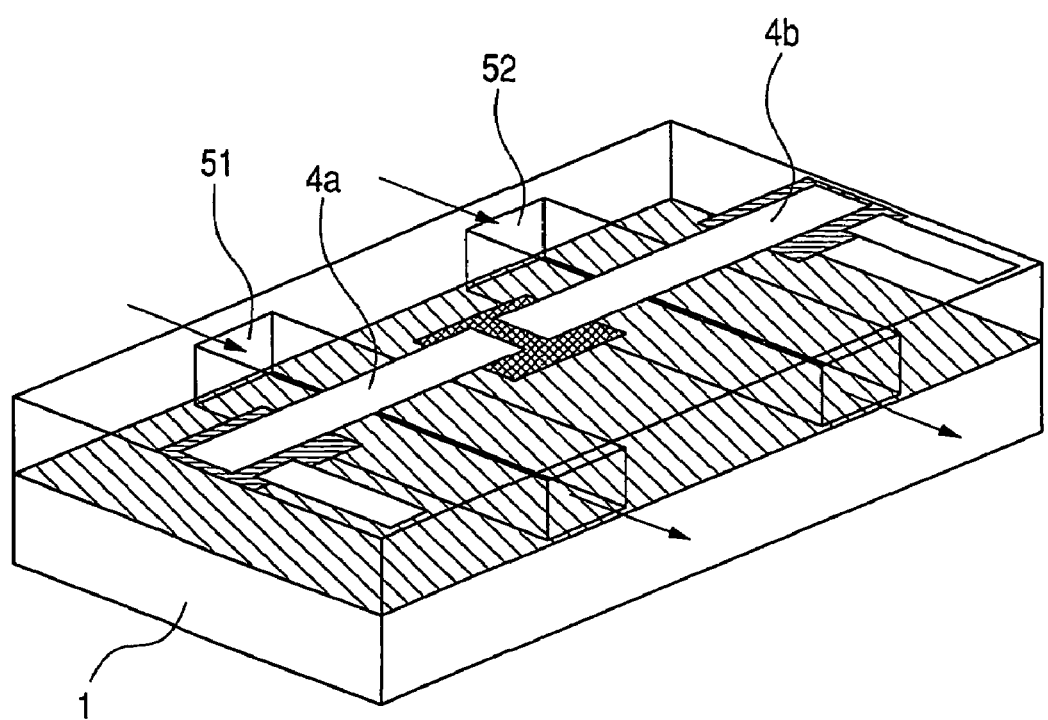
FIG. 5 is a perspective view showing a sensing device according to Example 4 of the present invention.

In the structure according to each of the examples described above, the test samples are applied to the surface of the substrate. Flow paths capable of successively performing the supply and discharge of test samples at high speed may be used. In Example 4, as shown in FIG. 5, a fundamental structure is identical to that in Example 1. Flow paths 51 and 52 are additionally provided to be orthogonal to the microstrip lines 4a and 4b, so test samples can be supplied thereto. In FIG. 5, the reference symbols and descriptions of the same constituent portions as that shown in FIG. 1 are omitted here except for part thereof.

In this example, at the time of examination, the samples are supplied through the flow paths 51 and 52 and then measurement is performed. After the completion of the measurement, the test samples can be discharged from the flow paths 51 and 52 by pushing the test samples. In this case, the test samples may be discharged by suction.

The laser beam application operation, the signal detection operation, and the like are performed as in Example 1. In this example, the test samples can be changed at high speed. Therefore, a plurality of test samples are measured using a single sensing device while the test samples are changed, so measurement time can be shortened.

Example 5

Figure 6:
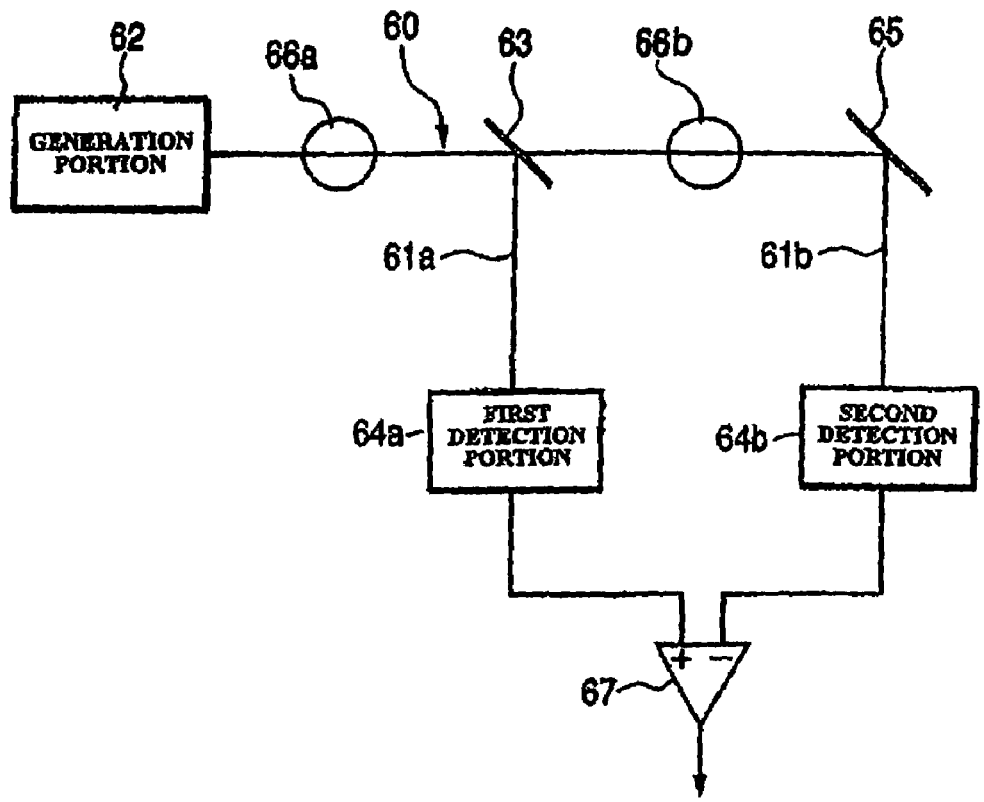
FIG. 6 is a block diagram showing a sensing device according to Example 5 of the present invention.

The electromagnetic wave transmitting portion including the plurality of transmission portions for propagating the electromagnetic waves therethrough can be composed of spaces. FIG. 6 shows an example in which the electromagnetic wave transmitting portion is composed of a first space portion 61a and a second space portion 61b which have a partially common portion 60. An electromagnetic wave from a generation portion 62 for generating the electromagnetic wave is divided into two waves by a beam splitter 63. One of the two waves propagates through the first space portion 61a and is detected by a first detection portion 64a. The other of the two waves propagates through the second space portion 61b through a reflecting mirror 65 and is detected by a second detection portion 64b. At this time, a reference test sample 66a is placed in the common space portion 60 between the generation portion 62 and the beam splitter 63 and a test sample 66b is placed in the second space portion 61b between the beam splitter 63 and the reflecting mirror 65. Even in such a structure, when a difference between outputs from the detection portions 64a and 64b is calculated by a comparator device 67, the same effect is obtained based on the same principle as that in each of the above-mentioned examples.

Example 6

Figure 7:
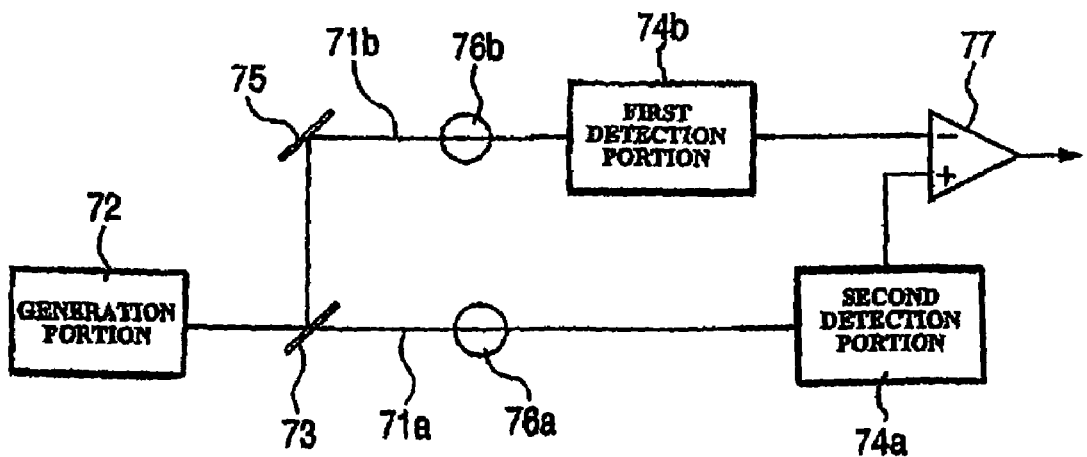
FIG. 7 is a block diagram showing a sensing device according to Example 6 of the present invention.
Figure 8:
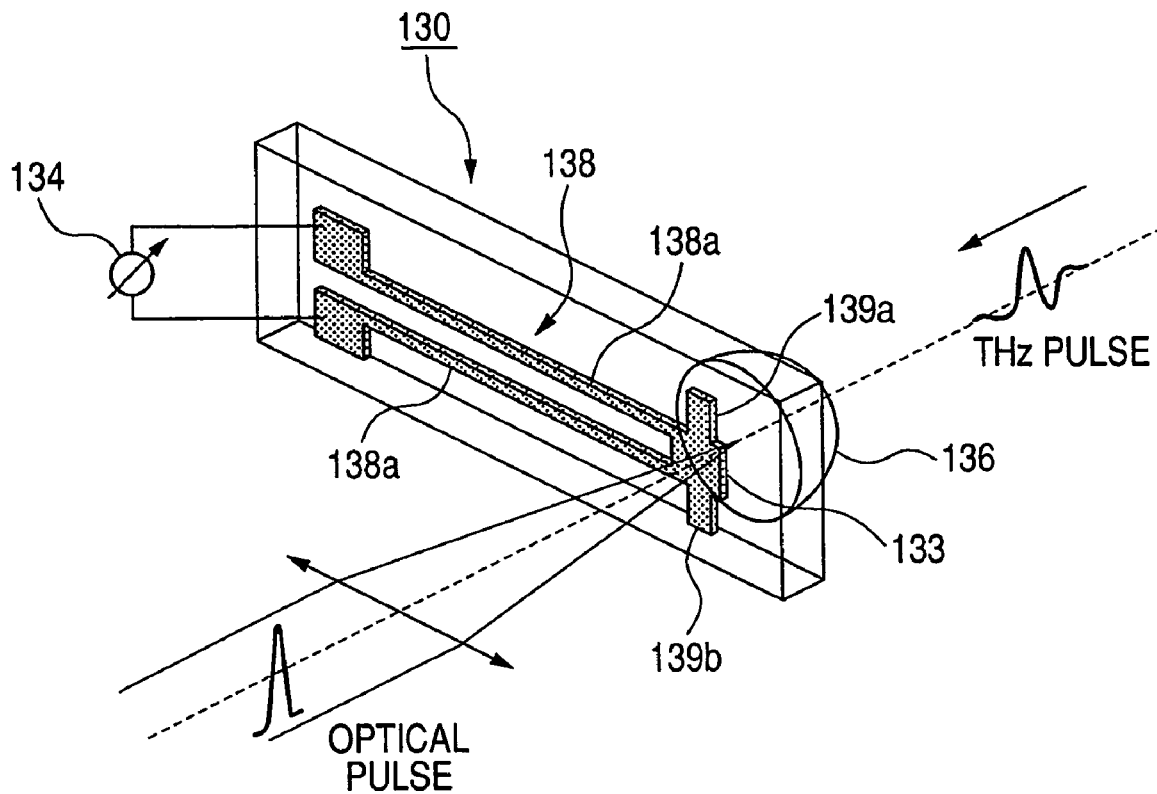
FIG. 8 shows an example of a conventional terahertz generation portion.
Figure 9:
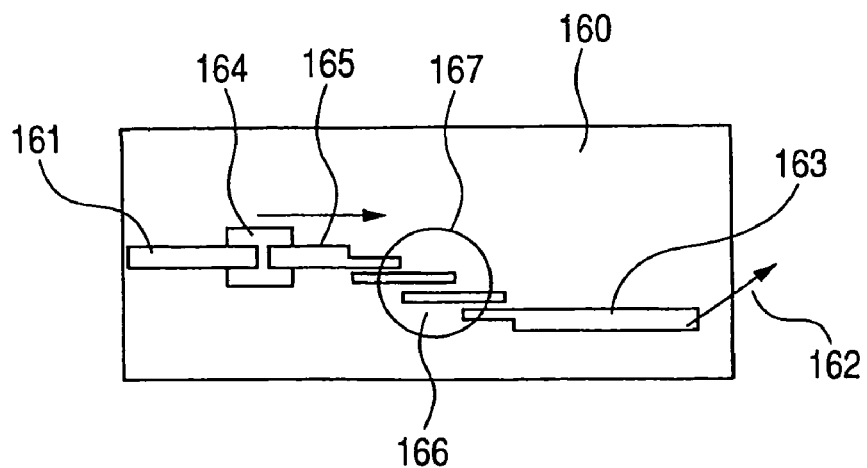
FIG. 9 shows a conventional example of terahertz transmission paths.

As shown in FIG. 7, the electromagnetic wave transmitting portion can be composed of a first space portion 71a and a second space portion 71b which are separately placed. In FIG. 7, reference symbols 72 denotes a generation portion for generating an electromagnetic wave, 73 denotes a beam splitter, 74a and 74b denote a first detection portion and a second detection portion, respectively, 75 denotes a reflecting mirror, 76a denotes a reference test sample, 76b denotes a test sample, and 77 denotes a comparator device. Even in such a structure, when a difference between outputs from the detection portions 74a and 74b is calculated by the comparator device 77, the same effect is obtained based on the same principle as that in the structural example shown in FIG. 6.

As many apparently widely different embodiments of the present invention can be made without departing from the spirit and scope thereof, it is to be understood that the invention is not limited to the specific embodiments thereof except as defined in the claims.

This application claims priority from Japanese Patent application No. 0.2005-248561 filed on Aug. 30, 2005, which is hereby incorporated by reference herein.

The invention claimed is:

1. A sensing device which uses an electromagnetic wave having a frequency in a frequency region of 30 GHz or more and 30 THz or less, comprising:

a dielectric substrate;

a generation portion provided on the dielectric substrate for generating the electromagnetic wave;

a first propagating portion provided on the dielectric substrate, wherein the first propagating portion is in contact with the generation portion for propagating the electromagnetic wave generated at the generation portion in a first direction;

a second propagating portion provided on the dielectric substrate, wherein the second propagating portion is in contact with the generation portion for propagating the electromagnetic wave generated at the generation portion in a second direction different from the first direction;

a first detection portion provided on the dielectric substrate for detecting the electromagnetic wave propagated through the first propagating portion; and a second detection portion provided on the dielectric substrate for detecting the electromagnetic wave propagated through the second propagating portion.

2. A sensing device according to claim 1, wherein the first and second propagating portions are placed to sandwich the generation portion along a straight line passing through the generation portion.

3. A sensing device according to claim 1, wherein the first and second propagating portions are electrodes for applying voltage to the generation portion.

4. A sensing device according to claim 1, wherein each of the first and second propagating portions is a metallic line, and the electromagnetic wave generated at the generation portion propagates along the metallic lines.

5. A sensing device according to claim 4, further comprising a metal conductive layer provided on a surface of the dielectric substrate opposite to a surface of the dielectric substrate on which the metallic lines are provided.

6. A sensing device according to claim 1, further comprising a differential unit for calculating a difference in intensity between the electromagnetic waves detected at the first and second detection portions respectively.

7. A sensing device according to claim 1, wherein the generation portion, the first detection portion and the second detection portion include photoconductive films.

* * * * *